United States Patent [19]

Leveen et al.

[11] Patent Number: 5,698,214

[45] Date of Patent: Dec. 16, 1997

[54] TREATMENT FOR MONILIAL VULVOVAGINITIS

[76] Inventors: Harry H. Leveen, 321 Confederate Cir.; Eric G. Leveen, 19 Palmetto Rd., both of Charleston, S.C. 29407; Robert F. Leveen, 815 S. 94th St., Omaha, Nebr. 68114

[21] Appl. No.: 840,196

[22] Filed: Feb. 24, 1992

[51] Int. Cl.$^6$ ........................................... A61K 9/02
[52] U.S. Cl. .......................... 424/430; 424/431; 424/433
[58] Field of Search .................... 424/430, 431, 424/433

[56] References Cited

U.S. PATENT DOCUMENTS

| | | | |
|---|---|---|---|
| 4,315,001 | 2/1982 | Blough | 536/1.1 |
| 5,110,801 | 5/1992 | Leveen et al. | 514/53 |

OTHER PUBLICATIONS

Floridi et al.; "Lonidamine, a Selective Inhibitor of Aerobic Glycolysis of Murine Tumor Cells"; pp. 497–499; *JNCI*, vol. 66, No. 3, Mar. 1981.

Ilinich et al.; "129240q Effect of Glucose and ATP on the Respiration of Ascitic Cancerous Cells in the Presence of Phlorizin and Ouabain"; p. 223; *Pharmacodynamics;* vol. 73, 1970.

Kolber et al.; "115099q Evidence for Carrier–Mediated Transport of Monosaccharides in the Ehrlich Ascites Tumor Cell"; p. 10834; *Chemical Abstracts;* vol. 67, 1967.

Walum et al.; "77012446 Kinetics of 2–deoxy–D–glucose Transport into Cultured Mouse Neuroblastoma Cells;" *Dialog Information Service Embase 74–79,* 1976.

Dozier et al.; "81246326 The Hexose Transport System in the Human K–562 Chronic Myelogenous Leukemia Derived Cell"; *Dialog Information Service Embase 80–81* (J. Cell. Physiol 1981).

Karnter and Ling; "Multidrug Resistance in Cancer"; *Scientific American,* pp. 44–51, Mar. 1989.

Warburg; "The Metabolism of Tumors", Richard R. Smith & Co., N.Y., 1931.

Warburg; "On the Origin of Cancer Cells"; p. 309; *Science,* vol. 123, No. 3191, Feb. 24, 1956.

Sussman et al; "Regulation of Cellular Engergy Metabolism"; p. 209; *Biochema et Biophysica Acta,* vol. 591, No. 209, 1980.

Hume et al.; "Role and Regulation of Glucose Metabolism in Proliferating Cells", *J. Nat. Can. Inst.,* vol. 62, No. 3, Jan., 1979.

Singh et al.; "Glucose Homeostasis in Rats Bearing a Transplantable Sarcoma", p. 3; *Cancer Res.,* vol. 40, No. 1699, May, 1980.

Waterhouse et al., "Glucogenesis from Alanine in Patients with Progressive Malignant"; p. 1968; *Cancer Res.,* vol. 39, No. 1968, Jun., 1979.

Waterhouse; "Lactate Metabolism in Patients with Cancer"; p. 66; *Cancer Res.;* vol. 33, No. 66, 1974.

Rowland; "Simultaneous Measurment of RNA, DNA, and Protein Synthesis in Mouse Tumor and Reticuloendothelial Tissue Slices Using Glucose–6–$^3$Rowland; Simultaneous Measurment of RNA, DNA, and Protein Synthesis in Mouse Tumor and Reticuloendothelial Tissue Slices Using Glucose–6–$^3$H as a Common Precursor"; p. 391, *Cancer Res.,* vol. 29; Feb., 1969.

Young; "Energy Metabolism and Requirements in the Cancer Patient"; p. 2336, *Cancer Res.,* vol. 37, Jul., 1977.

Fields et al., "Chronic Lactic Acidosis in a Patient with Cancer: Therapy and Metabolic Consequences"; p. 2026; *Cancer,* vol. 47, 1981.

Levin et al.; "Metabolic Alterations in Cancer"; p. 518, *SA Med J.,* vol. 59, Apr. 4, 1981.

Gold; "Cancer Cachexia and Gluconeogenesis"; *Ann NY Acad Sci,* vol. 72, p. 103, 1980.

Flier et al.; "Elevated Levels of Glucose Transport and Transporter Messenger RNA are Induced by ras or src Oncogenes"; *Science,* vol. 235, p. 1492, Mar. 20, 1987.

Lowry et al., "Diversity of Metabolic Patterns in Human Brain Tumors—I. High Energy Phosphate Compounds and Basic Composition"; *J. Neurochem,* vol. 29, p. 959, 1977.

Rousset et al., "Presence of Glycogen and Growth–related Variations in 58 Cultured Human Tumor Cell Lines of Various Tissue Origins"; *Can. Res.,* vol. 41; p. 1165, Mar., 1981.

Miko et al.; "Inhibiton of Energy Metabolism in Ehrlich Ascites Cells Treated with Dactylarin in Vitro"; *Can. Res.;* vol.39, p. 4242, Oct. 1979.

Newey et al.; "The Effect of Some Analogues of Phlorrhizin on Intestinal Hexose and Fluid Transfer"; *J. Physol;* vol. 169, p. 229, 1963.

Birnbaum et al.; "Transformation of Rat Fibroblasts by FSV Rapidly Increases Glucose Transporter Gene Transcription"; *Science,* vol. 235, p. 1495, Mar. 20, 1987.

Lotspeich; "Phlorizin and the Cellular Transport of Glucose"; *Harvey Lectures,* vol. 56, p. 63, 1961.

Chasis, et al.; "The Action of Phlorizin on the Excretion of Glucose, Xylose, Sucrose, Creatinine of Urea by Man"; *J. Clin. Invest.,* vol. 12, p. 1083, 1933.

Goldring et al.; "The Effects on Renal Activity of the Oral Administration of Phlorizin in Man"; *J. Clin. Invest.,* vol. 13, p. 749, 1934.

"Competition Between Phlorizin and Gold Thioglucose for Glucoreceptor Cell Transport Mechanisms in the Hypothalamus"; *Nutri Reviews,* vol. 33, p. 23, Jan. 1975.

(List continued on next page.)

*Primary Examiner*—Thurman K. Page
*Assistant Examiner*—James M. Spear
*Attorney, Agent, or Firm*—John S. Hale; Gipple & Hale

[57] ABSTRACT

Monilial Vulvovaginitis is treated by application of a composition containing one or more substances which inhibit glucose transfer into cells and cell metabolism. The composition of the invention is conveniently combined with a suitable carrier such as a non-aqueous gel and other therapeutically useful components.

8 Claims, No Drawings

OTHER PUBLICATIONS

Schulman et al.; "Hyperthermia: Its Effects on Proliferative and Plateau Phase Cell Cultures"; *Radiol.;* vol. 113. p. 209, 1974.

Harisladis, "Hyperthermia: Biological Studies at the Cellular Level"; *Radiol.,* vol. 117, p. 447, 1975.

Demetrakopoulos et al.; "Rapid Loss of ATP by Tumor Cells Deprived of Glucose: Contrast to Normal Cells"; *Biochem. and Biophysica. Res. Comm.;* vol. 82, p. 787, Jun. 14, 1978.

Gerner, et al; "A Transient Thermotolerant Survival Response Produced by Single Thermal Doses in HeLa Cells"; *Cancer Res.,* vol. 36, p. 1035, Mar., 1976.

Benedict et al.; "The Influence of Induced Diabetes on Malignant Tumors (Including a Report of a Case of Human Phlorhizin Glycosuria"; *Proc. Soc. for Experimental Biology & Medicine,* vol. 11, pp. 1913–1914 May 1912.

Wood et al.; "The Effect of Phlorhizin on Tumors in Animals"; *Proc. Soc. for Experimental Biology & Medicine;* vol. 11, p. 135 1915.

*Nature,* No. 4019, p. 663, Nov. 9, 1946.

Woodcock, "Isolation of Phloridzin from Apple Seeds"; *Nature,* vol. 159, p. 100, Jan. 8, 1947.

Woodcock, "Isolation of Phlorizin from Apple Seeds"; *Chem. Abst.,* vol. 41, p. 2859, 1947.

Weber; "Hexose Transport in Normal and in Rous Sarcoma Virus–transformed Cells"; *J. Bio Chem.,* vol. 218, No. 9, p. 2978, 1972.

Nash; "Phlorhizin Diabetes"; *Physiol. Review 7,* p. 385; 1927.

McKee et al.; "Phlorhizin Glucosuria"; *Physiol. Review 25* p. 255, 1945.

Reiffen et al.; "The Effect of Glucosome on the Proliferation and Energy Metabolism of in vitro Grown Ehrlich Ascites Tumor Cells"; *Z. Natureforch,* 36c, p. 255, 1981.

Zemplen et al.; "Sythesis of a Phloracetophenone Glucoside a Naringenin Glucoside and P–phlorizin"; *Chem. Abstr.,* vol. 36, p. 6163, 1942.

Leschke; "The Behavior of Phlorhizin after Extirpation of the Kidneys"; *Chem. Abst.,* p. 2506, 1910.

TREATMENT FOR MONILIAL VULVOVAGINITIS

BACKGROUND OF THE INVENTION

1. Field of the Invention

The present invention is directed to a composition and method for treating Monilial Vulvovaginitis by administering a pharmaceutically effective amount of one or more compounds which inhibit glucose transfer into cells. The compound is generally administered topically in a non-aqueous carrier such as a gel.

2. Description of Related Art

Monilial vulvovaginitis is ubiquitous and is occurring with ever increasing frequency. The weak immunological response to Candida infections is a partial reason, but one which has not changed and cannot be blamed for the recent increase of this infection. An aging population due to the prolongation of life has increased the incidence of senility. The absence of estrogen during senescence significantly decreases the vitality and glycogen content of the vaginal mucosa. Lactic acid production brought about by the action of Doderlein's bacillus on mucosal glycogen becomes minimal or absent lowering the resistance of the vagina to infection. Immunosuppression has become commonplace due to the liberal use of corticosteroids and non steroidal anti-inflammatory agents (NSAIDs). Infection in many of these patients is acquired from temporary immunosuppression during hospitalization, and must be considered nosocomial. Thirty four percent (34%) of normal people are asymptomatic carriers of *C. albicans*. Temporary immunosuppression in these people may initiate a candidal infection. Normal females using steroidal contraceptive drugs become more susceptible to candidal infections. The increasing incidence of diabetes in the population raises glucose concentrations in the blood and body secretions and stimulates the growth of Candida. Parental hyperalimentation in hospitalized patients involves prolonged elevations of blood glucose promoting moniliasis. Immunosuppressive drugs used to prevent rejection in transplanted organs and autoimmune diseases predispose to candidiasis. Since males are frequently carriers of Candida, multiple sex partners add to the possibilities for infection. Not the least important cause is the absence of inexpensive non toxic therapies which might be used prophylactically to suppress monilial vulvovaginitis in patients who are at high risk.

Candida requires specific nutriments for growth, all of which have been carefully investigated. A general requirement exists for phosphate, calcium, potassium, trace minerals, and some vitamins; but, careful inspection discloses a special need for nutriments to build a rapidly growing biomass. Candida do not require amino acids for this growth but merely a source of nitrogen such as ammonium salts since Candida are capable of synthesizing all the amino acids required for protein synthesis. (Miyashita S, Miwatana T, Fujino T, *Effects of Amino Acids on the Growth of C. albicans* Nutrition 1:45–49,50–60 1958) The major nutritional need is for a carbon source to create a positive carbon balance which would be required for any increase in cellular mass. In mammals, less than 1% of the dried body weight is in the form of a carbohydrate pool. By contrast, 50% of the dried weight of yeasts is carbohydrate. (Phaff H J In "The Yeasts" (Rose A H, Harrison J H eds) 1971 pp 135–210 Academic Press N.Y. also Manners D J In "The Yeasts" 1971 pp 419–440 Academic Press N.Y.) In tissue culture, the growth rate of Candida and other yeasts is linked directly to a carbon source usually in the form of carbohydrates. (Johnson, S A M *Candida Monilia: Effects of Amino Acids, Glucose, pH, Chlortetracycline, Aureomycin, Dibasic Sodium and Calcium Phosphates and Anaerobic Conditions on its Growth* Arch Derm Syphilol 1954 70:49–60) Candida and other yeasts can metabolize many types of hexoses, disaccharides and polysaccharides (Wickersham L J, Burton K A J Bacteriol 56:363 1948); yet the type of carbohydrate utilized by the yeast really depends on what is available in its living environment.

Drugs Presently Used for Vulvovaginal Candidiasis

Most of the present drugs used in the therapy of monilial vaginitis are polyene antibiotics. These drugs are produced by various species of Streptomyces which are grown in tissue culture. These drugs combine with sterols in the membranes of yeasts and increase the permeability of the cell thus provoking leakage of important intracellular substances. Their effectiveness depends on the sterol content of the membrane which varies in different species. Although resistant strains of Candida are not especially common, the clinical effectiveness of all antibiotics is impeded by the rapidity to which organisms develop resistance. Since the therapy of mycosis is usually long term, emergence of resistant strains are of considerable clinical importance. Athar has shown that various Candida species do develop resistance to polyene antibiotics. (Athar M A, Winner H I *The Development of Resistance by Candida Species to Polyene Antibiotics In Vitro* 1971 J Med Microbiol 44:505–517). Except for Amphotericin B, these antibiotics are too toxic for parenteral use. Fortunately, they are poorly absorbed and may be administered topically or orally. The most important members of this group are Nystatin and Amphotericin B. Resistant strains of Candida to Nystatin have been described in the medical literature. These preparations have the same defects as antibiotics used for bacterial infections including a narrow selective spectrum.

5-Flourocytosine was one of the early synthesized compounds originally intended to be a cytostatic agent, although this property has not been confirmed in animal studies. It is relatively nontoxic but experience discloses that effectiveness is limited and the development of resistance is common.

The imidazoles were known to be fungistatic since 1944. Subsequently, more than 100 benzimadazole derivatives have been subjected for their antimicrobial and pharmacological properties. Chlorabenzylimadazole (chlormidazole) is the most active of the benzimadazole derivatives and is fairly well tolerated. It has antifungal properties against yeasts and dermatophytes, but this activity is dramatically lowered by the presence of serum and protein. Of the imidazole compounds, only clotrimazole, miconazole, econazole, fluconazole and ketoconazole are clinically useful for the treatment of yeast infections. The imidazoles inhibit synthesis of protein and RNA. The inhibition is brought about by membrane leakage with resultant loss of ionic potassium and phosphate. Although the imidazoles are fungistatic at moderate concentrations, they are less so in the presence of blood, serum and exudation caused by infection.

Present drugs used for vulvovaginal candidiasis are included in the above listings. Unfortunately, these drugs were found by happenstance and derivatized by intention. No consideration was given to design drugs which might seriously interfere with the metabolism and nutrition of the yeast cells, but pharmaceutical companies embarked on an expensive time consuming quest to isolate antibiotics from mold cultures which, in the past, have only fortuitously produced successful antibiotics.

SUMMARY OF THE INVENTION

In accordance with the present invention, a composition and methodology is provided for treating Monilial Vulvovaginitis by administering one or more substances which inhibit glucose transfer into cells, such as phloretin, phlorizin and cytochalasin B. These substances can be combined with known polyene antibiotics and imidazoles to achieve an unexpected synergistic effect. Typically, the composition of the invention is combined with a suitable carrier, which is typically non-aqueous in an amount of 8 to 25 mg of inhibitor per ml of carrier.

The invention and its various embodiments will, however, be better understood by first having reference to some of the technical considerations which form the basis for the present invention.

DESCRIPTION OF THE PREFERRED EMBODIMENT

In human candidal vulvovaginitis, the only carbohydrate available to the yeast cell is glucose. Therefore, any media representative of the vaginal habitat should contain glucose as the limiting carbon source. Chloramphenicol may be added to suppress the growth of bacteria since the growth of yeasts is not inhibited by chloramphenicol. The composition of media used in the present invention for the growth of yeast is contained in a manuscript by Fiechter. (Fiechter A, Fuhramann G F, Kappeli O. *Advances in Microbial Physiology* 1981 22:123) As long as a culture medium is carbon limited, cellular volume will increase linearly as the concentration of the carbon source is increased. As soon as a different nutrient in the media becomes limiting, the growth of the biomass levels off. Thus, it becomes possible to determine the maximum concentration of carbon source which renders the media carbon limited. (Fiechter A, Kappeli O Meussdoerffer F *Batch and Continuous Culture in the Yeast* pp 108 vol. 2 ed. by Rose A H & Earrison J S Academic Press London 1987) A modified Wickerham medium contains glucose as the carbon source. (Wickerham, L J 1951 Technical Bulletin No. 1029 U.S. Dept. Agriculture, Washington, D.C.).

Since glucose is the limiting source for the cellular growth in the human vagina and in culture media, it is essential that the kinetics of glucose transport across the membrane of Candida be completely understood. Only then can it be determined whether interference in membrane transfer might control the rate of yeast cell growth.

It has now been proven and universally accepted that glucose enters the interior of the yeast cell by a constitutive facilitated diffusion system. (Cooper T J *Transport in Sacrharomyces cereviseiae* in "The molecular Biology of the Yeast Saccharaomyces" 1982 ed. by Strathern J N, Jones E W, Broach J R, pp. 403–408 Cold Spring Harbor Laboratory N.Y. 1982) The transport of hexoses in yeast by involving a facilitated diffusion system with a membrane protein carrier makes high capacity uptake of glucose possible. (Lienhard G E, Slt W, et al *How Cells Absorb Glucose* Scientif Amer 226:86–91 1992) It is high uptake rate which facilitates the cellular growth of Monilia. Monilia can dramatically increase its biomass in transfer of different types of sugars and discloses a marked proclivity for glucose. (Kotyk A, and Janacek K *Cell Membrane Transport* pp 341 Plenum Press, N.Y. 1975) Burger investigated a number of different saccharides and concluded that they all utilize the same carrier and could produce competitive interference with one another. (Burger M, Kejmova L, Kleinzeller A *Transport of Somemono and disaccharides into Yeast Cells* Biochem J 71:233 1959) Others have found that non metabolizable glucose analogues such as L sorbose and D Xylose inhibit Glucose utilization by 90–85% (Kotyk A, *Properties of the Sugar Carrier in Baker's Yeast Folia* Microbiol 1967 12:121) Cirillo confirmed that non metabolizable glucose analoguss were competitive inhibitors of glucose uptake. (Cirillo V P *Mechanism of Glucose Transport Across Yeast Cell Membrane* J Bacteriol 1962 84:485) Also, the kinetics of glucose transport were found to be identical to what is observed in human erythrocytes. Later, Cirillo found that non-utilizable sugars such as 2 methoxy-D glucose markedly diminished the transport of glucose across the cell membrane of Baker's yeast. What was also noticed is that the pattern of selectivity for Baker's yeast was surprisingly similar to that described for human erythrocytes. (Cirillo V *Relationship Between Sugar Structure and Competition for the Sugar Transport System in Baker's Yeast* J Bacteriol 1968 95: 603–611) It is apparent that the glucose carrier system is very similar or almost identical to that seen in animal cells.

Theoretical information confirms that to strike at the fundamental metabolism of *Monilia albicans* attention should be focused on carbohydrate metabolism. The metabolism of yeasts is primarily focused on the synthesis utilization of carbohydrates unlike animal cells where the structural and metabolic activity is concerned with proteins. The invention is primarily concerned with the manipulation of glucose metabolism to control the growth of monilial cells, since the metabolic interface that yeasts share with animal metabolism is mainly with glucose. Cirillo has pointed out the similarity in glucose transfer which yeasts share with human erythrocytes. LeFevre has found that glucose transfer across erythrocytes is antagonized by a number of compounds which reversibly attach themselves tO the glucose carrier protein with greater affinity than does glucose and other hexoses. (LeFevre P G, *Sugar Transport in the Red Blood Cell: Structure Activity Relationships in Substrate and Antagonists* Pharmacol Rev 1961 13:39:75) The principal antagonists to glucose transfer are phlorizin and its agulcone phloretin. Over the years, the activity of phloretin and phlorizin in animal cells has been well investigated. (Lotspeich W D Phlorizin and the Cellular Transport of Glucose Harvey Lectures 56:63–91; McKee F W, Hawkins W B *Phlorizin Glucosuria* Physiol Rev. 25:255–280 1945) Yet, these compounds are a scientific curiosity without known pharmacologic use. Cytochalasin B which is a mold metabolite actively attaches itself to the glucose transfer protein of cells. This aggressive attachment of radio-labeled Cytochalasin B to the glucose transfer protein of cells is used to measure the number of glucose transfer sites on cell membranes. LeFevre mentions in his Pharmacological Reviews article mentioned above that dillyl stilbesterol and 3,3' di2-chlorallyl stilbesterol are 1000 times more active in blocking glucose entry into erythrocytes than phloretin and phlorizin. Since this compound possesses less estrogenic activity than diethyl stilbesterol, it is suitable for use in monilial vulvovaginitis to block glucose entry into the yeast cells. The scientific literature contains no information on whether inhibitors of glucose transfer would inhibit the growth of the growth of Candida. Experiments were undertaken to show ascertain whether significant inhibition would appear.

EXAMPLES

A liquid culture medium was prepared with using glucose as the carbon source (10 Grams/liter) and ammonium sulfate as the nitrogen source (5 grams/liter) and containing vitamins, trace minerals and salts and the amino-acids methionine, tryptophan and histidine. (Ready mixed formulation available from Difco Laboratories, Detroit Mich. to which glucose is added.) To 100 of sterile culture media in an Erlenmeyer flask, 0.1 ml of a growing culture of *monilia albicans* was added after shaking to insure an even suspension in the medium. Sterile air was bubbled though each flask to insure constant aeration. It was calculated from the cell counts that approximately 260,000 yeast cells were added. After 36 hours of growth at 37° C., 10 ml of the culture was removed with a pipette after agitation to insure an even suspension and transferred into a centrifuge tube. The tube was centrifuged for 30 minutes at 500 G. Five cultures were used for each experiment and the results averaged. There were eight different groups each using the growing culture as described above. To 5 control flasks, nothing was added. To five other control tubes 0.25 ml of following substances were added: A.) 25 mg. cytochalasin B dissolved in 0.25 ml of propylene glycol; B.) 50 mg. Phloretin dissolved in 0.25 ml of propylene glycol; C.) 25 mg. of Phloretin dissolved in 0.25 ml of propylene glycol; D.) 10 mg. of Phloretin dissolved in 0.25 ml of propylene glycol: E.) 100 mg. of phlorizin dissolved in 0.25 mg propylene glycol; F.) 50 mg. of 2 methoxy D glucose plus 0.25 ml of propylene glycol and G.) 50 mg. 5, thio D glucose plus 0.25 ml of propylene glycol. The amount of solids in the control tubes with polyethylene glycol was averaged and expressed as 100. The amounts in each experimental tube is expressed as a percentage of the control tube.

The following results were obtained:

| Control tubes with propylene glycol | 100% |
|---|---|
| Control tube without propylene glycol | 104% |

This result was taken to mean that propylene glycol had no effect on the growing culture since there was no statistical difference between the two groups and the results were within the limits of the experiment.

The results of the experimental tubes were:

| Control tubes with proplyene glycol | 100% |
|---|---|
| Cytochalasin B 25 mg. | 8% |
| Phloretin 50 mg. | 6% |
| Phloretin 25 mg. | 5% |
| Phloretin 10 mg. | 13% |
| Phlorezin 100 mg. | 8% |
| 2, methoxy D glucose | 3% |
| 5, thio D glucose | 6% |

These results indicate that chemicals which inhibit glucose entry into yeast cells and/or interfere with the metabolism of glucose inhibit the growth of Monilia in tissue culture.

The growth of Candida in the culture was measured to ascertain the minimal inhibitory concentration of Nystatin. The minimal inhibitory dose of phloretin was then found to be 1.65 mg/dl. When these two drugs were mixed together and added to the growth mixture, the inhibition of growth was found to be 76% in excess of the sum of the individual inhibitions. Such a result can only be due to unexpected synergism. Similar results were obtained using ketoconizole in place of nystatin. Thus, it must be concluded that the presence of glucose blockers enhances the activity of both imidazole and polyene antibiotics beyond what would expect on a mere additive basis.

For topical use, the chemicals mentioned above must have carriers to dissolve or suspend them being cognizant of easy insertion. It was decided that a suppository or sponge carrier would be an ideal method for topical insertion. In choosing the carrier, it is wise to bear in mind that Candida is an aquatic yeast and will not grow without water. Therefore, as little water and secretions should be available as is practical. Water accounts for 80–90% of the weight of a cell and the chemical biochemical reactions which take place inside the cell require an aqueous environment. Water activity has been used to characterize the free water activity in the environment. (Brown A D Bacteriological Reviews 40:803 1976 also Brown, A D Advances in Microbial Physiology 17:181 1978) Bowever, it may be more appropriate to measure free water by similarity as determined by vapor pressure of the aqueous medium inside and outside the cell which measures. Considerable literature sustains the observation that many yeasts are unable to grow in high concentrations of dissolved substances. For these reasons, acrilamides have been included in the formulations of carrier substances. Suppositories containing 25 to 50 mg of active glucose inhibitors are placed in a 2–3 ml. volume of propylene glycol, adding sufficient acrylamide to formulate a stiff gel suitable for suppository insertion. Another method to apply the medicament is by using the medicament as a solid core in an open cell hydrophlilic polyurethane foam. (Hypo™ manufactured by W.R. Grace is a suitable polyurethane foam.) A polycarboxylated vinyl polymer (Carbopol™ manufactured by B.F. Goodrich) has also been used as a thickening agent and a substrate to acidify the vagina. Other hydrophilic colloids such as the hydroxy cellulose derivatives are also suitable hydrocolloids.

In foregoing description, the invention has been described with reference to a particular preferred embodiment, although it is to be understood that specific details shown are merely illustrative, and the invention may be carried out in other ways without departing from the true spirit and scope of the following claims:

We claim:

1. A pharmaceutical composition for topically treating Monilial Vulvovaginitis which comprises a composition comprising a pharmaceutically effective amount of one or more substances which inhibit glucose entry into Moniliai cells by action on the cell membrane and interfere with glucose metabolism in said cells and an additional synergistically effective amount of at least one substance selected from the group consisting of imidazoles and polyene antibiotics in a pharmaceutically acceptable carrier.

2. A method for the treatment of Monilial Vulvovaginitis which comprises: a) mixing a pharmaceutically effective amount of a substance or substances which inhibit glucose entry into cells in a pharmaceutically acceptable carrier; and b) topically administering to a subject said pharmaceutically effective amount of a substance or substances in said pharmaceutically acceptable carrier to inhibit glucose entry into Monilial cells and interfere with glucose metabolism in Monilial cells to inhibit the growth of Monilial cells.

3. The method of claim 2 wherein said carrier is a non-aqueous gel.

4. The method of claim 2 wherein said substance or substances is selected from the group consisting of phloretin, phlorizin, cytochalasin B, dillyl stilbesterol and nonutilizable sugars.

5. The method of claim 2 wherein said substance or substances is combined with said pharmaceutically acceptable carrier in an amount ranging from about 8 to 25 mg per ml of carrier.

6. The method of claim 2 in which said substance or substances is combined with a synergistically effective amount of an additional substance selected from the group consisting of imidazoles and polyene antibiotics to enhance the actions of imidazoles and polyene antibiotics.

7. The method of claim 2 in which said substance or substances is administered by means of a tampon or suppository containing said substance or substances in a carrier.

8. The method of claim 2 wherein said pharmaceutically acceptable carrier is selected from a group consisting of propylene glycol, polycarboxylated vinyl polymer and hydroxy cellulose derivatives.

* * * * *